US009695202B2

(12) United States Patent
Henning et al.

(10) Patent No.: US 9,695,202 B2
(45) Date of Patent: Jul. 4, 2017

(54) ORGANOMODIFIED SILOXANES HAVING PRIMARY AMINO FUNCTIONS, NOVEL ORGANOMODIFIED SILOXANES HAVING QUATERNARY AMMONIUM FUNCTIONS AND THE METHOD FOR THE PRODUCTION THEREOF

(71) Applicant: EVONIK DEGUSSA GMBH, Essen (DE)

(72) Inventors: Frauke Henning, Essen (DE); Wilfried Knott, Essen (DE); Horst Dudzik, Essen (DE)

(73) Assignee: Evonik Degussa GmbH, Essen (DE)

( * ) Notice: Subject to any disclaimer, the term of this patent is extended or adjusted under 35 U.S.C. 154(b) by 82 days.

(21) Appl. No.: 14/548,724

(22) Filed: Nov. 20, 2014

(65) Prior Publication Data

US 2015/0080593 A1 Mar. 19, 2015

Related U.S. Application Data

(62) Division of application No. 13/521,351, filed as application No. PCT/EP2010/070855 on Dec. 29, 2010, now abandoned.

(30) Foreign Application Priority Data

Feb. 3, 2010 (DE) ........................ 10 2010 001 531

(51) Int. Cl.
*C07F 7/18* (2006.01)
*C08G 77/388* (2006.01)

(52) U.S. Cl.
CPC .......... *C07F 7/1804* (2013.01); *C08G 77/388* (2013.01)

(58) Field of Classification Search
CPC .... C08G 11/388; C08G 77/388; C07F 7/1804
USPC .................................................. 556/418, 423
See application file for complete search history.

(56) References Cited

U.S. PATENT DOCUMENTS

| | | | |
|---|---|---|---|
| 5,371,161 A | 12/1994 | Knott | |
| 5,384,340 A | 1/1995 | Hara et al. | |
| 5,430,166 A | 7/1995 | Klein et al. | |
| 5,430,167 A | 7/1995 | Klein et al. | |
| 5,455,367 A | 10/1995 | Klein et al. | |
| 5,475,127 A | 12/1995 | Klein et al. | |
| 5,981,812 A | 11/1999 | Eufinger et al. | |
| 6,255,511 B1 | 7/2001 | Klein et al. | |
| 6,291,622 B1 | 9/2001 | Dröse et al. | |
| 6,307,082 B1 | 10/2001 | Klein et al. | |
| 6,489,498 B2 | 12/2002 | Klein et al. | |
| 6,858,663 B2 | 2/2005 | Knott et al. |
| 7,018,458 B2 | 3/2006 | Knott et al. |
| 7,125,585 B2 | 10/2006 | Dudzik et al. |
| 7,157,541 B2 | 1/2007 | Knott et al. |
| 7,196,153 B2 | 3/2007 | Burkhart et al. |
| 7,598,334 B2 | 10/2009 | Ferenz et al. |
| 7,612,158 B2 | 11/2009 | Burkhart et al. |
| 7,612,159 B2 | 11/2009 | Burkhart et al. |
| 7,619,035 B2 | 11/2009 | Henning et al. |
| 7,645,848 B2 | 1/2010 | Knott et al. |
| 7,754,778 B2 | 7/2010 | Knott et al. |
| 7,825,205 B2 | 11/2010 | Knott et al. |
| 7,825,206 B2 | 11/2010 | Neumann et al. |
| 7,825,209 B2 | 11/2010 | Knott et al. |
| 7,931,747 B2 | 4/2011 | Weyershausen et al. |
| 8,138,294 B2 | 3/2012 | Henning et al. |
| 2002/0161158 A1 | 10/2002 | Burkhart et al. |
| 2007/0128143 A1 | 6/2007 | Gruning et al. |
| 2008/0004357 A1 | 1/2008 | Meyer et al. |
| 2008/0125503 A1 | 5/2008 | Henning et al. |
| 2009/0137751 A1 | 5/2009 | Knott et al. |
| 2009/0137752 A1 | 5/2009 | Knott et al. |
| 2010/0022435 A1 | 1/2010 | Henning et al. |
| 2010/0029587 A1 | 2/2010 | Brückner et al. |
| 2010/0041629 A1 | 2/2010 | Giessler-Blank et al. |
| 2010/0041910 A1 | 2/2010 | Schubert et al. |
| 2010/0071849 A1 | 3/2010 | Knott et al. |
| 2010/0081781 A1 | 4/2010 | Schubert et al. |
| 2010/0105843 A1 | 4/2010 | Knott et al. |
| 2010/0113633 A1 | 5/2010 | Henning et al. |
| 2010/0168367 A1 | 7/2010 | Schubert et al. |
| 2010/0184913 A1 | 7/2010 | Ebbrecht et al. |
| 2010/0249339 A1 | 9/2010 | Henning et al. |
| 2010/0292357 A1 | 11/2010 | Knott et al. |
| 2010/0298455 A1 | 11/2010 | Henning et al. |
| 2011/0021693 A1 | 1/2011 | Henning et al. |
| 2011/0034576 A1 | 2/2011 | Henning et al. |
| 2011/0042004 A1 | 2/2011 | Schubert et al. |
| 2011/0046305 A1 | 2/2011 | Schubert et al. |
| 2011/0172373 A1 | 7/2011 | Knott et al. |

(Continued)

FOREIGN PATENT DOCUMENTS

| | | |
|---|---|---|
| EP | 1 956 038 | 8/2008 |
| GB | 2 185 984 | 8/1987 |
| JP | 59-69110 A | 4/1984 |
| JP | 62-185091 A | 8/1987 |
| JP | 63-51314 A | 3/1988 |
| JP | 5-295272 A | 11/1993 |
| JP | 2008-31481 A | 2/2008 |
| JP | 2013-517337 A | 5/2013 |

OTHER PUBLICATIONS

International Search Report Issued Feb. 1, 2011 in PCT/EP10/70855 Filed Dec. 29, 2010.

(Continued)

*Primary Examiner* — Porfirio Nazario Gonzalez
(74) *Attorney, Agent, or Firm* — Philip P. McCann; Smith Moore Leatherwood LLP

(57) ABSTRACT

The invention relates to a method for producing siloxanes selectively carrying primary amino groups by reacting them with ammonia, and to compounds produced in this way.

7 Claims, No Drawings

(56) References Cited

U.S. PATENT DOCUMENTS

| | | |
|---|---|---|
| 2011/0230619 A1 | 9/2011 | Kuppert et al. |
| 2011/0230633 A1 | 9/2011 | Ferenz et al. |
| 2011/0245412 A1 | 10/2011 | Schubert et al. |
| 2011/0281973 A1 | 11/2011 | Schubert et al. |
| 2011/0301254 A1 | 12/2011 | Knott et al. |
| 2011/0306694 A1 | 12/2011 | Glos et al. |
| 2012/0010302 A1 | 1/2012 | Hartung et al. |
| 2012/0027704 A1 | 2/2012 | Henning et al. |
| 2012/0046486 A1 | 2/2012 | Henning et al. |
| 2012/0097883 A1 | 4/2012 | Henning et al. |
| 2012/0190760 A1 | 7/2012 | Henning et al. |
| 2012/0190762 A1 | 7/2012 | Hubel et al. |
| 2012/0308494 A1 | 12/2012 | Schubert et al. |

OTHER PUBLICATIONS

Japanese Office Action issued Mar. 10, 2014 in Patent Application No. 2012-551525 (English Translation only).

Dow Corning, Silicones in Pharmaceutical Applications, 2001, Dow Corning Corporation, pp. 1-21, (24 pages in all, including Title page, blank page and concluding page.).

ORGANOMODIFIED SILOXANES HAVING PRIMARY AMINO FUNCTIONS, NOVEL ORGANOMODIFIED SILOXANES HAVING QUATERNARY AMMONIUM FUNCTIONS AND THE METHOD FOR THE PRODUCTION THEREOF

This application is a divisional application of U.S. Ser. No. 13/521,351 filed on Jul. 10, 2012, which is a 371 application of PCT/EP2010/070855 filed on Dec. 29, 2010.

The invention relates to novel organomodified siloxanes having primary amino functions and novel organomodified siloxanes having quaternary ammonium functions and the method for the production thereof.

The production both of silanes and of organomodified polysiloxanes having primary amino functions is described in the prior art by reference to the variety of synthesis routes.

Aminoalkyl-functional alkoxysilanes are used as adhesion promoters in coatings or adhesives and sealants. They are produced by the platinum(0)-catalyzed hydrosilylation of allyl chloride, as is described, for example, in DE 10104966 A1. On account of secondary reactions, propene, chloropropane and propylchlorosilane are formed, meaning that distillative purification of the product is required. The haloalkyl function of the 3-chloropropylchlorosilanes obtained in this way can, according to EP 1273612 A1, be further functionalized in diverse ways, for example by reaction with ammonia, hydrogen sulfide, alkali metal or ammonium sulfides, rhodanides and also methacrylates. By means of an alcoholysis, the functional chlorosilanes can be converted to the corresponding alkoxysilanes.

For the more efficient production of aminoalkyl-functional alkoxysilanes, in the prior art, instead of the three-stage chlorosilane route, the direct hydrosilylation of allylamine with ethoxy hydrogen silanes is described. However, this synthesis route has turned out to be difficult on account of the strong inhibition of the transition metal catalyst by the complexing allylamine. A series of patent applications demonstrates the attempts to find an economical hydrosilylation method with the help of specific ruthenium or rhodium catalysts and also nitrogen and phosphorus compounds as cocatalysts, thus, for example, U.S. Pat. No. 4,481,364, U.S. Pat. No. 4,867,501, U.S. Pat. No. 4,921,988, U.S. Pat. No. 4,927,953 or U.S. Pat. No. 5,001,246. The methods often require large amounts of catalyst and lead, on account of rearrangements of the double bonds and limited addition reaction selectivities, to product mixtures consisting of the branched alpha and beta and also the linear gamma isomer of the aminopropylsilane. The silane mixtures have to be purified by distillation before further use. On account of the comparatively large amounts of catalyst and the yield losses caused by the secondary reactions, and the required distillative purification, the hydrosilylation of allylamine is associated with high costs.

Aminopropylalkoxysilanes can be converted to polysiloxanes by means of hydrolysis and condensation reactions. On account of the basic amino function, preference is given to using alkaline catalysts such as, for example, KOH, ammonium hydroxide or carboxylate. EP 1580215 A1 and the specifications cited therein may be incorporated herewith as reference. This synthesis route has limits. In the case of the synthesis of amino-functional polysiloxanes with a high functionality density, the price of the expensive special silane is increasingly driving the material costs upwards and, at the same time, the yield is reduced by the amount of alcohol liberated during the hydrolysis. In the case of basically catalyzed equilibrium reactions of polysiloxanes with amino groups, silazanes can also arise as by-products.

To increase the regioselectivity and avoid the formation of silazane during the hydrosilylation of unsaturated amines with hydrogen siloxanes, use is made, according to DE 4436077 A1, of protective group technology, which requires two additional synthesis steps. Good selectivities during the hydrosilylation of allylamine with tetramethyldisiloxane are described in U.S. Pat. No. 5,026,890 A1 using the Karstedt catalyst. Nevertheless, comparatively large amounts of at least 40 ppm of platinum are required by this platinum(0)-divinyltetramethyldisiloxane complex.

To produce methacrylamide-functional alkylsilanes, US 20050176911 A1 describes the reaction of epoxy-functional alkylsilanes with methanolic ammonia solution at 0° C. to 25° C. over 1 to 3 days. A subsequent derivatization with methacryloyl chloride leads to the target compounds. EP 1956038 A1 discloses a similar method for producing terminally methacrylamide-functional linear polydimethylsiloxanes. Mixed-substituted polysiloxanes having additional functional groups are not mentioned.

EP 1008614 A2 claims linear polydimethylsiloxanes, the chain ends of which are SiC-linked with in each case one allyl polyether and one alkanolamine or alkanolalkylamine. The production takes place from a linear, epoxy- and polyether-functional polydimethylsiloxane by titanium-catalyzed epoxide ring opening for example with diethanolamine at 80° C. Polysiloxanes having primary amino functions cannot be produced by the described methods and are neither specified nor claimed.

US 2008/0314518 A1 describes the reaction of amino-functional silanes or of ethylenediamine in situ with glycidoxypropyltriethoxysilane for producing an aqueous two-component adhesion promoter. The crosslinking required for good adhesion is ensured since an amino function reacts with more than one of the epoxide rings added in excess.

The prior art discloses siloxanes with not more than two amino functions and often without further functional groups. Amino-functional siloxanes and in particular their charged derivatives, which are accessible by reaction of the amino function with various acids or else also by their alkylation to give quaternary nitrogen compounds, have a marked electrostatic affinity towards surfaces and consequently provide for good substantivity of the compounds. The substantivity of the aminosiloxane, being its ability to anchor itself electrostatically to substrates, is associated with its functionality density, i.e. with the number of uncharged or else also charge-carrying nitrogen functions based on the molecular weight. Committed to the objective of providing aminosiloxanes with freely selectable substantivity, it is noticed that the prior art hitherto lacks selective and cost-effective synthetic accesses to siloxanes which contain more than just one or two primary amino functions per siloxane chain.

As is known from the production of alkanolamines, the epoxide ring opening with ammonia does not stop at the stage of the primary amine. The primary and secondary amines formed are relatively strong nucleophiles and compete with the ammonia to react with the epoxide ring. (Literature: Ullmann's Encyclopedia of Industrial Chemistry, Release 2006, 7$^{th}$ Edition, Wiley VCH). The amino-functional polysiloxanes described in EP 1008614 A2 are low molecular weight and have only one terminal amino function per chain. EP 1956038 A1 likewise describes only linear terminal amino-functional intermediates. Consecutive reactions of the primary amines formed lead in the first instance to chain extension and not to a gelation as a result of crosslinking. As soon as the siloxane has lateral substituents and particularly when more than two amino functions are to be linked to the siloxane, a further reaction of the primary and secondary amines leads to comparatively large viscosity increases. The gelation risk increases with increasing molar mass of the product and also, associated therewith, with increasing product viscosity. Moreover, secondary amines are toxicologically unacceptable since they form carcinogenic nitrosamines with nitrites or nitrous gas oxides from the air.

One object of the present invention consists in producing siloxanes having primary amino functions and further organomodifications in a selective and cost-effective manner. The aim is to ensure a high yield of primary amino functions while simultaneously avoiding the formation of secondary amines.

One advantage of the methods described in EP 1956038 A1 and US 20050176911 A for reacting epoxy-functional compounds with ammonia is the long reaction times of at least 12 hours ranging to 3 days. The longer the reaction lasts and the lower the local concentration of ammonia, the more preferentially the formed primary amines react in subsequent reactions with the remaining epoxy functions, resulting in gelation. The long reaction times result inevitably from the selected process parameters of pressure and temperature.

A further object of the present invention furthermore consists in developing a cost-effective method for producing siloxanes with a high chemoselectivity for the formation of primary amino groups.

DESCRIPTION OF THE INVENTION

Surprisingly, it has been found that the reaction of laterally epoxy-modified siloxanes with ammonia produces siloxanes carrying selectively primary amino groups without crosslinkages via secondary or tertiary amine formation taking place.

The invention therefore provides a method for producing selectively primary amino group-carrying siloxanes by reacting laterally epoxy-modified siloxanes with gaseous, dissolved or in situ generated ammonia.

This is surprising and unforeseeable for the person skilled in the art since alkyl-substituted amines are relatively strong nucleophiles and thus favor further reactions of the desired product with other epoxide rings to form secondary amines over the primary reaction. This is true in particular for the case of a high functionality density and thus a high concentration of epoxide groups in the system.

A further object of the present invention consists in modifying siloxanes not only at the chain ends, but also laterally with primary amino functions in order to achieve higher functionality densities.

The invention provides siloxanes of the general formula 1

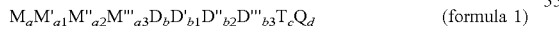   (formula 1)

where
M=$(R^1_3SiO_{1/2})$
M'=$(R^2R^1_2SiO_{1/2})$
M''=$(R^3R^1_2SiO_{1/2})$
M'''=$(R^4R^1_2SiO_{1/2})$
D=$(R^1_2SiO_{2/2})$
D'=$(R^2R^1SiO_{2/2})$
D''=$(R^3R^1SiO_{2/2})$
D'''=$(R^4R^1SiO_{2/2})$
T=$(R^5SiO_{3/2})$
Q=$(SiO_{4/2})$ a=0 to 32; preferably 1 to 22, in particular 2;
a1=0 to 10, preferably 1 to 5, in particular 2;
a2=0 to 32; preferably 1 to 22, in particular 2;
a3=0 to 10; preferably 1 to 5, in particular 2;
b=0 to 600, preferably 10 to 500, in particular 20 to 400;
b1=0 to 50, preferably 0.1 to 20, in particular 2 to 10;
b2=0 to 50, preferably 0.1 to 20, in particular 1 to 10;
b3=0 to 50, preferably 1 to 20, in particular 2 to 10;
c=0 to 20, preferably 0 to 10, in particular 0;
d=0 to 20, preferably 0 to 10, in particular 0;
with the proviso that
if a1=2, b1≠0 and/or b2≠0 and/or b3≠0 and/or a2≠0 and/or a3≠0 and preferably at least two of the factors a2, a3, b1, b2 and b3≠0.

$R^1$ independently of the others, is identical or different linear or branched hydrocarbon radicals having 1 to 30 carbon atoms or else aromatic hydrocarbon radicals having 6 to 30 carbon atoms, preferably methyl or phenyl, in particular methyl;

$R^2$ independently of the others, is identical or different organic radicals which carry a primary amino function, preferably radicals which, in addition to the amino function, carry a hydroxyl group, in particular selected from the group

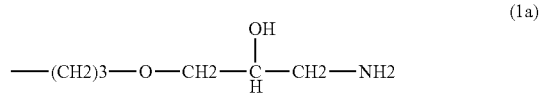 (1a)

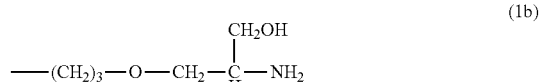 (1b)

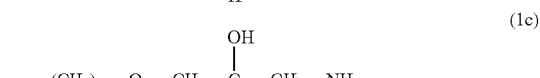 (1c)

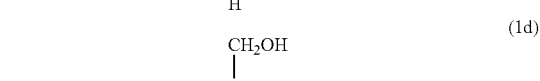 (1d)

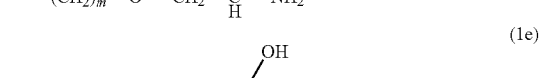 (1e)

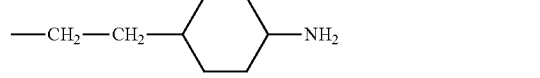 (1f)

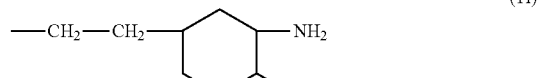 (1g)

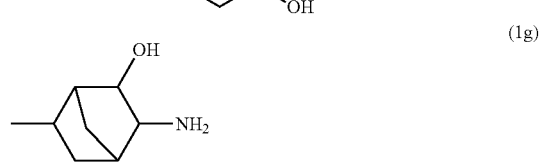 (1h)

 (1i)

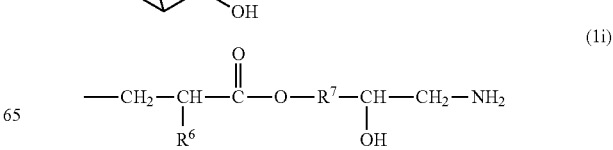

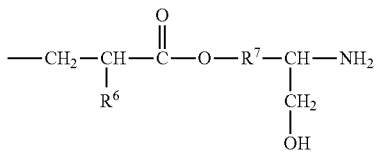

(1j)

where
- $R^6$ is identical or different radicals from the group hydrogen or alkyl having 1 to 6 carbon atoms, preferably methyl radicals,
- $R^7$ is identical or different divalent hydrocarbon radicals which optionally contain ether functions and which are optionally polyoxyalkylene radicals, preferably methylene radicals and
- m is an integer from 2 to 18,
- $R^3$ is identical or different radicals from the group
  —$CH_2$—$CH_2$—$CH_2$—O—($CH_2$—$CH_2$O—)$_x$—($CH_2$—$CH(R')$O—)$_y$—R"
  —$CH_2$—$CH_2$—O—($CH_2$—$CH_2$O—)$_x$—($CH_2$—$CH(R')$O—)$_y$—R"
  —$CH_2$—$CH_2$—(O)$_{x'}$—$R^{IV}$
  —$CH_2$—$CH_2$—$CH_2$—O—$CH_2$—$CH(OH)$—$CH_2OH$
  or
  —$CH_2$—$CH_2$—$CH_2$—O—$CH_2$—$C(CH_2OH)_2$—$CH_2$—$CH_3$, in which
- x is 0 to 100, preferably >0, in particular 1 to 50,
- x' is 0 or 1,
- y is 0 to 100, preferably >0, in particular 1 to 50,
- R' independently of the others, is an alkyl or aryl group having 1 to 12 carbon atoms which is optionally substituted, for example substituted with alkyl radicals, aryl radicals or haloalkyl or haloaryl radicals, where, within a radical $R^4$ and/or a molecule of the formula 1, mutually different substituents R' may be present, and
- R" independently of the others, is a hydrogen radical or an alkyl group having 1 to 4 carbon atoms, a group —C(O)—R'" where R'"=alkyl radical, a group —$CH_2$—O—R', an alkylaryl group, such as e.g. a benzyl group, the group —C(O)NH—R',
- $R^{IV}$ is an optionally substituted, e.g. halogen-substituted, saturated or unsaturated hydrocarbon radical having 1 to 50, preferably 3 to 30, carbon atoms, in particular a decyl, dodecyl, tetradecyl or hexadecyl radical,
- $R^4$ independently of the others, is identical or different linear, cyclic or branched, optionally olefinically unsaturated or aromatic hydrocarbon radicals having 1 to 30 carbon atoms which may be substituted with the groups containing the heteroatoms O, N, S, P or halogen atoms and which preferably contain no primary or secondary amine functions, preferably alkanol radicals, carboxylic acid radicals or carboxylic acid ester radicals, in particular hydrocarbon radicals having 5 to 30 carbon atoms, such as, for example, a dodecenyl, tetradecyl, hexadecyl or octadecyl radical and
- $R^5$=independently of the others, identical or different radicals $R^1$, $R^2$, $R^3$ or $R^4$, preferably $R^1$, in particular methyl, phenyl, dodecyl or hexadecyl.

The various monomer units of the building blocks given in the formulae (siloxane chains or polyoxyalkylene chain) can be constructed blockwise among one another with any desired number of blocks and be based on an arbitrary sequence or a statistical distribution. The indices used in the formulae are to be regarded as statistical average values.

The invention further provides ionic adducts of the amino-functional siloxanes according to the invention with protic reactants $H^+A^-$. The adduct is present in the form of —$NH_3^+A^-$. The anions $A^-$ are identical or different counterions to the positive charges on the protonated, primary amino groups, selected from inorganic or organic anions of the acids $H^+A^-$, and also derivatives thereof. Preferred anions are, for example, chloride, sulfate and hydrogensulfates, carbonate and hydrogencarbonate, phosphate and hydrogenphosphates, acetate and homologous carboxylates with linear or branched, saturated or olefinically unsaturated alkyl chains, aromatic carboxylates, carboxylates formed from amino acids, citrates, malonates, fumarates, maleates, substituted and unsubstituted succinates and carboxylates formed from L-hydroxycarboxylic acids, such as, for example, lactate. The aminosiloxanes according to the invention and their ionic adducts can be present in dissociation equilibria depending on the stability of the adduct formed.

Moreover, the invention provides the quaternary ammonium compounds deriving from the alkylation of the primary amine function of the formula 2

$$M_a M''''_{a1} M''_{a2} M'''_{a3} D_b D''''_{b1} D''_{b2} D'''_{b3} T_c Q_d \quad \text{(formula 2)}$$

where
- M=($R^1_3SiO_{1/2}$)
- M''''=($R^8R^1_2SiO_{1/2}$)
- M''=($R^3R^1_2SiO_{1/2}$)
- M'''=($R^4R^1_2SiO_{1/2}$)
- D=($R^1_2SiO_{2/2}$)
- D''''=($R^8R^1SiO_{2/2}$)
- D''=($R^3R^1SiO_{2/2}$)
- D'''=($R^4R^1SiO_{2/2}$)
- T=($R^5SiO_{2/2}$)
- Q=($SiO_{4/2}$)
- a, a1, a2, a3, b, b1, b2, b3, c and d have the meaning given above, the radicals $R^1$, $R^3$, $R^4$ and $R^5$ likewise satisfy the definition given above and
- $R^8$ independently of the others, is identical or different organic radicals which carry ammonium functions; suitable radicals $R^8$ are, for example, preferably identical or different radicals selected from the group

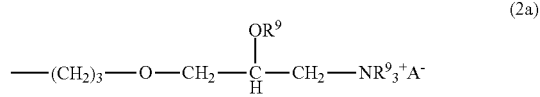

(2a)

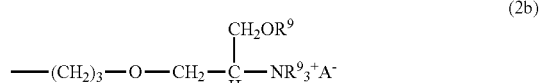

(2b)

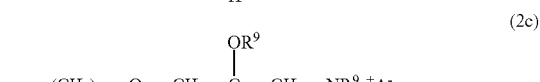

(2c)

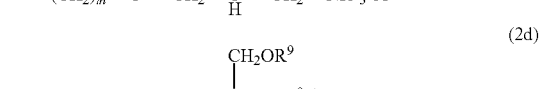

(2d)

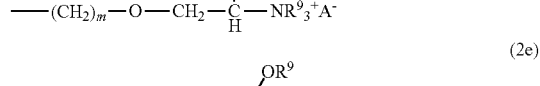

(2e)

-continued

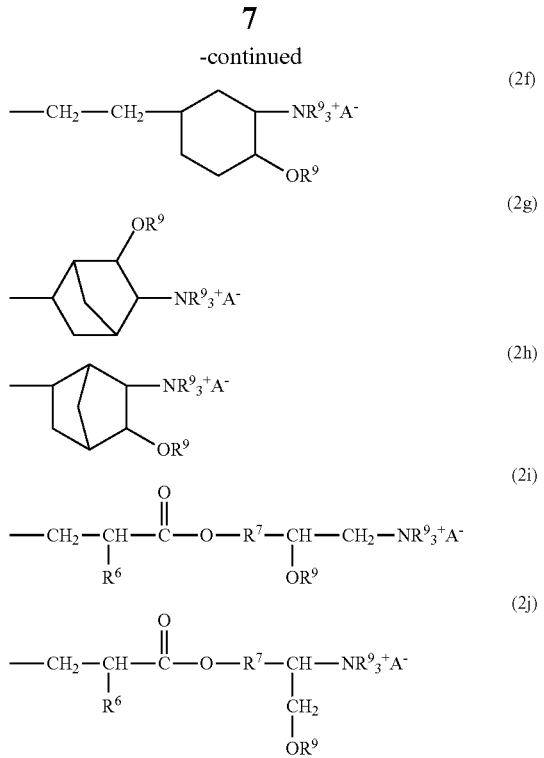

(2f)
(2g)
(2h)
(2i)
(2j)

$R^9$ independently of the others, is identical or different linear or branched hydrocarbon radicals having 1 to 30 carbon atoms or aromatic hydrocarbon radicals having 6 to 30 carbon atoms, preferably methyl or ethyl.

To produce the compounds according to the invention having quaternary ammonium functions, the compounds of the formula 1 according to the invention are reacted with the alkylating reagents. For this, alkylating reagents known to the person skilled in the art, such as e.g. alkyl halides or dialkylsulfates, in particular, can be used.

The invention furthermore provides preparations in the form of solutions, emulsions, dispersions and/or mixtures comprising the compounds according to the invention of the formulae 1 or 2. These preparations can comprise further additives and accessory materials, for example, but not limited to those selected from the group of fillers, emulsifiers, dyes, pigments.

The invention further provides the use of the amino-functional siloxanes of the formulae 1 or 2 according to the invention as emulsifier for cosmetic preparations, compatibilizer for plastic blends, release agent, hydrophobicizing agent, dispersant for colored pigments and fillers, additives for textile finishing (softeners), conditioner for hair, primer for surface coating/adhesion promoter, additive for corrosion protection formulations, PU foam stabilizer, antifoam and/or as wetting agent.

The invention further provides the method for producing the aminosiloxanes of the formula 1 according to the invention.

Method for the Production of the Siloxanes According to the Invention:

The compounds of formula 1 according to the invention are produced from epoxy-functional compounds of the formula 3

$$M_a M''''_{a1} M''_{a2} M'''_{a3} D_b D''''_{b1} D''_{b2} D'''_{b3} T_c Q_d \quad \text{(formula 3)}$$

where
$M = (R^1_3 SiO_{1/2})$
$M'''' = (R^{10} R^1_2 SiO_{1/2})$
$M'' = (R^3 R^1_2 SiO_{1/2})$
$M''' = (R^4 R^1_2 SiO_{1/2})$
$D = (R^1_2 SiO_{2/2})$
$D'''' = (R^{10} R^1 SiO_{2/2})$
$D'' = (R^3 R^1 SiO_{2/2})$
$D''' = (R^4 R^1 SiO_{2/2})$
$T = (R^5 SiO_{3/2})$
$Q = (SiO_{4/2})$ a, a1, a2, a3, b, b1, b2, b3, c and d have the meaning given above, the radicals $R^1$, $R^3$, $R^4$ and $R^5$ likewise satisfy the definition specified above and $R^{10}$ independently of the others, is identical or different organic epoxy radicals.

Suitable epoxy radicals $R^{10}$ are, for example, preferably identical or different radicals selected from the group

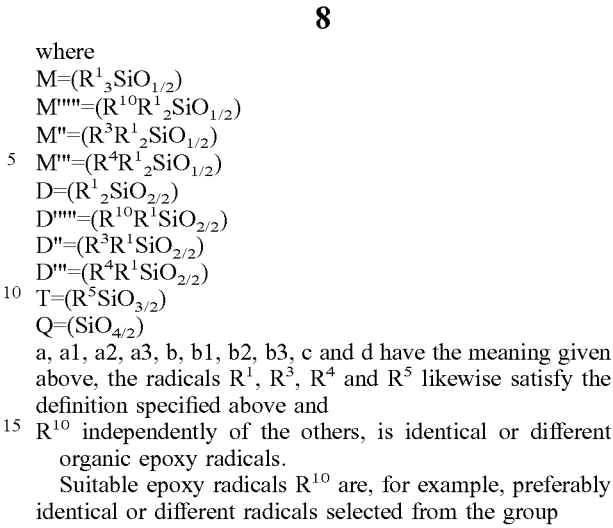

(3a)
(3b)
(3c)
(3d)
(3e)

The epoxy-functional siloxanes, which can also carry further substituents, are produced as described in the prior art—for example in EP 0415208 A2—by means of transition metal-catalyzed hydrosilylation. The ring-opening reaction is then carried out with the introduction of ammonia, with or without using solvents, at atmospheric pressure or in the autoclave at superatmospheric pressure. The ammonia can also be generated in situ from compounds which cleave off ammonia, for example when increasing the temperature.

A large number of customary solvents is suitable for the production according to the invention of the amino-functional siloxanes. Depending on the polarity of the epoxy-functional preproduct, the solvent is selected according to its dissolving capacity for starting material and product. The solvent should behave largely inertly both towards ammonia and also towards the epoxy-functional preproduct under the selected reaction conditions. Thus, for example, aromatic hydrocarbons, but also ethers or alcohols are suitable. Preference is given to using toluene, xylene, methanol, ethanol, propanol and its isomers, in particular 2-propanol.

When using autoclaves, higher reaction temperatures of up to 150° C., preferably 60° C. to 130° C., can be established since the reaction gas remains in the closed system. When the autoclave is opened and charged, without pressure, for example with saturated ammoniacal solution, the pressure build-up in the closed autoclave during heating can be in the range from 1 to 50 bar, preferably 5 to 20 bar. If a closed pressurized reactor is charged with ammonia gas via a gassing device, a pregiven pressure of 1 to 50 bar, preferably from 5 to 20 bar, can be established during the charging. In this case, the reaction times can be 1 to 10 hours, preferably 1 to 5 hours.

A particular advantage of the method at pressures greater than 1 bar and at temperatures above 50° C. is that, compared to the prior art, it is possible to realize shorter reaction times of less than 12 hours. The higher local concentration of ammonia in the dissolved phase, moreover, influences the selectivity in a positive manner since the ratio of ammonia to the formed primary amine, i.e. of the reagents competing for the ring openings, is increased in favor of the ammonia. Preferred process pressures are in the range from 2 to 50 bar, in particular 5 to 20 bar.

A further advantage of the higher reaction temperature is evident in the case of the reaction of relatively high molecular weight epoxy siloxanes. The viscosity of the starting compounds is reduced at higher temperatures, which facilitates the mixing and the mass transfer and thus likewise brings about a rapid reaction. Since, in the pressureless method, the higher reaction temperature likewise brings about a more rapid degassing of the ammonia, it may be advantageous to work on a small scale with a gas frit and on a production scale with a bubble-column reactor.

If the reaction is carried out without pressure, then a minimum temperature of 50° C., preferably of 60° C., is required for a rapid reaction with acceptable selectivity. For pressureless reaction control, it may be advantageous to increase the rate of the epoxy ring opening by means of suitable catalysts. Heterogeneous or homogeneous catalysts from the area of acids, Lewis acids or bases, and also metal salts or complexes, or transition metal salts or complexes can be used.

The reaction can be carried out in a one-pot method or continuously. When the reaction is complete, the product is distilled off in order to remove residual ammonia and optionally also the solvent used. The pH can be adjusted by means of solid or dissolved buffer systems. If a pH adjustment is carried out with solid salts, a filtration step then follows. In the event of product clouding arising, a filtration does not necessarily have to take place.

Ammonia can be used as a reagent not only in molecularly gaseous form or in the form of a saturated solution, but can also be used in chemically bonded form. Thus, for example, as well as gaseous ammonia or aqueous or alcoholic ammonia solutions, it is also possible to use amine and/or ammonium compounds which release ammonia at elevated temperatures with decomposition or else during hydrolysis in solution, such as, for example, ammonium halides, ammonium carbonate and/or hydrogencarbonate, ammonium sulfate and/or hydrogensulfate, ammonium sulfamate, ammonium phosphate, hydrogenphosphate and/or dihydrogenphosphate, ammonium cyanate, ammonium carboxylates such as, for example, ammonium acetate, ammonium hydrogenoxalate and/or oxalate, ammonium hydrogencitrate, ammonium benzoate, ammonium formate, ammonium carbamate, ammonium lactate, ammonium tartrate or ammonium succinate. Furthermore, ammonia can be generated in situ from hydroxylamine, hydroxylamine-O-sulfonic acid or amidosulfonic acid or urotropin (hexamethylenetetramine) by decomposition under the selected reaction conditions. Depending on the amine or ammonium compound used, as a result of secondary reactions on the amine function formed, carboxamides or carbamates can be formed, and/or as a result of secondary reactions on the hydroxyl function formed, carboxylic acid esters or corresponding sulfuric acid esters or phosphoric acid esters can be formed.

WORKING EXAMPLES

In the examples listed below, the present invention is described for the purposes of illustrating the invention, without any intention of limiting the invention, the scope of application of which arises from the entire description and the claims, to the embodiments specified in the examples. Where ranges, general formulae or compound classes are given below, then these are intended to encompass not only the corresponding ranges or groups of compounds that are explicitly mentioned, but also all part ranges and part groups of compounds which can be obtained by removing individual values (ranges) or compounds. Where, within the context of the present description, documents are cited, then their content, in its entirety, should be deemed as belonging to the disclosure content of the present invention. Where, within the context of the present invention, compounds such as e.g. organomodified polysiloxanes are described which can have different monomer units several times, then these can occur in these compounds in random distribution (random oligomer) or in an ordered manner (block oligomer). Data relating to the number of units in such compounds is to be understood as meaning statistical average values, averaged over all of the corresponding compounds.

Example 1 (According to the Invention)

In a 500 ml four-neck flask with attached precision-ground glass stirrer, reflux condenser and internal thermometer, 83.7 g of an allylpolyethylene glycol with an average molecular weight of 409 g/mol are heated with 7.21 g of allyl glycidyl ether (>99% purity, Sigma Aldrich) and 159.1 g of a poly(methylhydrogen)dimethylsiloxane copolymer with a hydrogen fraction of 1.27 val/kg to 50° C. with stirring. 5 ppm of platinum in the form of a platinum(0) catalyst modified as in EP 1520870 are added using a syringe and the reaction temperature is increased to 70° C. The conversion, determined gas volumetrically is quantitative after 2 hours. Distillation on a rotary evaporator at 10 to 20 mbar and 140° C. gives a clear, liquid product with an epoxide content of 0.32% by weight of epoxide oxygen.

In a 500 ml four-neck flask with attached precision-ground glass stirrer, reflux condenser with bubble counter and internal thermometer, ammonia is introduced into a solution of 100 g of ethanol and 1.0 g of 1-methylimidazole (99%, Sigma Aldrich) and, at 50° C. with stirring, 100 g of the epoxy-functional polyethersiloxane are added dropwise via a dropping funnel over a period of 1.5 hours. When the metered addition is complete, ammonia is introduced for a further 4 hours at 50° C. Distillation on a rotary evaporator at 70° C. and 10 to 20 mbar gives a yellow, liquid product with an amine content of 0.2% by weight of primary amine nitrogen (theoretical 0.27%, 74% yield), <0.01% by weight of secondary amine nitrogen and 0.14% by weight of tertiary amine nitrogen (theoretical 0.16% by weight from methylimidazole).

Example 2 (According to the Invention)

In a 500 ml four-neck flask with attached precision-ground glass stirrer, reflux condenser and internal thermometer, 97.5 g of 1-hexadecene (purity 93%, Chevron Philipps Chemical Company) are heated with 25.5 g of allyl glycidyl ether (>99% purity, Sigma Aldrich) and 150.0 g of a poly(methylhydrogen)dimethylsiloxane copolymer with a hydrogen fraction of 3.51 val/kg to 70° C. with stirring. 5 ppm of platinum in the form of a platinum(0) catalyst modified as in EP 1520870 are added using a syringe and stirred at 70° C. The conversion, determined gas volumetrically, is 80% after 4.5 hours. A further 5 ppm of platinum catalyst are added until, after 10.5 hours, 99.5% conversion is achieved. Distillation on a rotary evaporator at 10 to 20 mbar and 140° C. gives a clear, liquid product with an epoxide content of 1.12% by weight of epoxide oxygen.

In a 330 ml steel autoclave with magnetic stirrer fish and manometer, 100 g of the epoxy siloxane are dissolved in 200 g of 2-propanol. Using a dry ice/ethanol cooling bath, the autoclave together with the contents is cooled to −70° C. and the solution is saturated with ammonia by passing it through for 30 minutes. The autoclave is closed and heated to 120° C. (external oil bath temperature) with stirring, during which the pressure increases to 10 bar. After a reaction time of 4 hours, the autoclave is aerated and the solvent is distilled off on a rotary evaporator at 80 to 90° C. and 10 to 20 mbar. This gives a clear, yellowish product with an amine content of 0.79% by weight of primary amine nitrogen (theoretical 0.97%, 81% yield), <0.01% by weight of secondary amine nitrogen and <=0.01% by weight of tertiary amine nitrogen.

Example 3 (According to the Invention)

In a 2 l four-neck flask with attached precision-ground glass stirrer, reflux condenser and internal thermometer, 243.2 g of an allylpolyoxyalkylene glycol end-capped at the terminal hydroxy group by acetylation and having an average molecular weight of 874 g/mol and a composition, by weight, of 80% propylene oxide and 20% ethylene oxide, 759.4 g of an allylpolyoxyalkylene glycol end-capped at the terminal hydroxy group by acetylation and having an average molecular weight of 4094 g/mol and a composition, by weight, of 58% propylene oxide and 42% ethylene oxide, 49.0 g of allyl glycidyl ether (>99% purity, Sigma Aldrich) and 300.0 g of a poly(methylhydrogen)dimethylsiloxane copolymer with a hydrogen fraction of 2.29 val/kg are heated to 50° C. with stirring. 5 ppm of platinum in the form of a platinum(0) catalyst modified as in EP 1520870 are added using a syringe and stirred at 70° C. The conversion, determined gas volumetrically, is 100% after 2.5 hours. Distillation on a rotary evaporator at 10 to 20 mbar and 140° C. gives a clear, liquid product with a viscosity of 2555 mPa*s at 25° C. and an epoxide content of 0.44% by weight of epoxide oxygen.

In a 330 ml steel autoclave with gassing stirrer and manometer, 100 g of the polyether- and epoxy-functional siloxane are dissolved in 200 g of 2-propanol. Using a dry ice/ethanol cooling bath, the autoclave together with the contents is cooled to −70° C. and the solution is saturated with ammonia by passing it through for 30 minutes. The autoclave is closed and heated to 80° C. (external oil bath temperature) with stirring, during which the pressure increases to 16 bar. After a reaction time of 4 hours at 80° C., the autoclave is aerated and the solvent is distilled off on a rotary evaporator at 70° C. and 10 to 20 mbar. This gives a slightly cloudy, yellowish product with a viscosity of 3309 mPa*s at 25° C. and an amine content of 0.34% by weight of primary amine nitrogen (theoretical 0.38%, 90% yield), <0.01% by weight of secondary amine nitrogen and <=0.01% by weight of tertiary amine nitrogen.

Example 4 (According to the Invention)

In a 2 l four-neck flask with attached precision-ground glass stirrer, reflux condenser and internal thermometer, 227.6 g of an allylpolyoxyalkylene glycol methyl ether with an average molecular weight of 818 g/mol and a composition, by weight, of 80% propylene oxide and 20% ethylene oxide, 713.4 g of an allylpolyoxyalkylene glycol methyl ether with an average molecular weight of 3846 g/mol and a composition, by weight, of 58% propylene oxide and 42% ethylene oxide, 49.0 g of allyl glycidyl ether (>99% purity, Sigma Aldrich) and 300.0 g of a poly(methylhydrogen)dimethylsiloxane copolymer with a hydrogen fraction of 2.29 val/kg are heated to 50° C. with stirring. 5 ppm of platinum in the form of a platinum(0) catalyst modified as in EP 1520870 are added using a syringe and stirred at 70° C. The conversion, determined gas volumetrically, is 100% after 2.5 hours. Distillation on a rotary evaporator at 10 to 20 mbar and 140° C. gives a clear, liquid product with a viscosity of 2954 mPa*s at 25° C. and an epoxide content of 0.42% by weight of epoxide oxygen.

In a 330 ml steel autoclave with gassing stirrer and manometer, 100 g of the polyether- and epoxy-functional siloxane are dissolved in 200 g of 2-propanol. Using a dry ice/ethanol cooling bath, the autoclave together with the contents is cooled to −70° C. and the solution is saturated with ammonia by passing it through for 30 minutes. The autoclave is closed and heated to 80° C. (external oil bath temperature) with stirring, during which the pressure increases to 10 bar. After a reaction time of 6 hours at 80° C., the autoclave is aerated and the solvent is distilled off on a rotary evaporator at 70° C. and 10 to 20 mbar. This gives a slightly cloudy, yellowish product with a viscosity of 3209 mPa*s at 25° C. and an amine content of 0.35% by weight of primary amine nitrogen (theoretical 0.36%, 97% yield), <0.01% by weight of secondary amine nitrogen and <=0.01% by weight of tertiary amine nitrogen.

Example 5 (According to the Invention)

In a 330 ml steel autoclave with gassing stirrer and manometer, 100 g of a poly(methyl(2-cyclohexenyl oxide)ethyl)dimethylsiloxane copolymer with a viscosity of 160 mPa*s at 25° C. and an epoxide content of 1.9% by weight of epoxide oxygen are dissolved in 200 g of 2-propanol. Using a dry ice/ethanol cooling bath, the autoclave together with the contents is cooled to −70° C. and the solution is saturated with ammonia by passing it through for 30 minutes. The autoclave is closed and heated to 80° C. (external oil bath temperature) with stirring, during which the pressure increases to 10 bar. After a reaction time of 6 hours at 80° C., the autoclave is aerated and the solvent is distilled off on a rotary evaporator at 70° C. and 10 to 20 mbar. This gives a slightly cloudy, yellowish product with a viscosity of 182 mPa*s at 25° C. and an amine content of 1.30% by weight of primary amine nitrogen (theoretical 1.63%, 80% yield), <0.01% by weight of secondary amine nitrogen and 0.03% by weight of tertiary amine nitrogen.

Example 6 (According to the Invention)

In a 2 l four-neck flask with attached precision-ground glass stirrer, reflux condenser and internal thermometer, 17.4 g of methyl 10-undecenoate (96% purity, Sigma Aldrich), 10.0 g of allyl glycidyl ether (>99% purity, Sigma Aldrich) and 200.0 g of a poly(methylhydrogen)dimethylsiloxane copolymer with a hydrogen fraction of 0.7 val/kg are heated to 70° C. with stirring. 5 ppm of platinum in the form of a platinum(0) catalyst modified as in EP 1520870 are added using a syringe and stirred at 70° C. The conversion, determined gas volumetrically, is 24.7% after 2.5 hours. A further 5 ppm of Pt are added and the mixture is stirred for a further 2 hours, which increases the conversion to 45.6%. A further 10 ppm of Pt are added and the mixture is further stirred at an elevated reaction temperature of 100° C. After a further two hours, the conversion is 80.0% and, after a total of 10.5 hours is 97.1%. Distillation on a rotary evaporator at 10 to 20 mbar and 140° C. gives a clear, slightly brownish, liquid product with a viscosity of 189.6 mPa*s at 25° C. and an epoxide content of 0.49% by weight of epoxide oxygen.

In a 330 ml steel autoclave with gassing stirrer and manometer, 100 g of the carboxylic acid ester- and epoxy-functional siloxane are dissolved in 200 g of 2-propanol. Using a dry ice/ethanol cooling bath, the autoclave together with the contents is cooled to −70° C. and the solution is saturated with ammonia by passing it through for 30 minutes. The autoclave is closed and heated to 80° C. (external oil bath temperature) with stirring, during which the pressure increases to 8 bar. After a reaction time of 6 hours at 80° C., the autoclave is aerated and the solvent is distilled off on a rotary evaporator at 70° C. and 10 to 20 mbar. This gives a slightly cloudy, brownish product with a viscosity of 227.1 mPa*s at 25° C. and an amine content of 0.48% by weight of primary amine nitrogen (theoretical 0.43%), <0.01% by weight of secondary amine nitrogen and 0.04% by weight of tertiary amine nitrogen.

The invention claimed is:

1. A method for producing selectively primary amino group-carrying siloxanes of general formula 1 or a quaternary ammonium derivative thereof, wherein $$M_a M'_{a1} M''_{a2} M'''_{a3} D_b D'_{b1} D''_{b2} D'''_{b3} T_c Q_d \quad \text{(formula 1)}$$

where
$M=(R^1{}_3SiO_{1/2})$;
$M'=(R^2R^1{}_2SiO_{1/2})$;
$M''=(R^3R^1{}_2SiO_{1/2})$;
$M'''=(R^4R^1{}_2SiO_{1/2})$;
$D=(R^1{}_2SiO_{2/2})$;
$D'=(R^2R^1SiO_{2/2})$;
$D''=(R^3R^1SiO_{2/2})$;
$D'''=(R^4R^1SiO_{2/2})$;
$T=(R^5SiO_{3/2})$;
$Q=(SiO_{4/2})$;
a is in a range of from 0 to 32;
a1 is in a range of from 0 to 10;
a2 is in a range of from 0 to 32;
a3 is in a range of from 0 to 10;
b is in a range of from 0 to 600;
b1 is in a range of from 0.1 to 50;
b2 is in a range of from 0.1 to 20;
b3 is in a range of from 0 to 50;
c is in a range of from 0 to 20; and
d is in a range of from 0 to 20;
wherein:
if a1=2, at least one of b1, b2, b3, a3 is not 0 and at least two of the factors a2, a3, b1, b2 and b3 are not 0;
$R^1$ is each independently a linear or branched hydrocarbon radical having 1 to 30 carbon atoms or aromatic hydrocarbon radicals having 6 to 30 carbon atoms;
$R^2$ is each independently an organic radical comprising a primary amino function;
$R^3$ is each independently a radical selected from the group consisting of
—$CH_2$—$CH_2$—$CH_2$—O—($CH_2$—$CH_2$O—)$_x$—($CH_2$—$CH(R')$O—)$_y$—R'',
—$CH_2$—$CH_2$—O—($CH_2$—$CH_2$O—)$_x$($CH_2$—$CH(R')$O—)$_y$—R'',
—$CH_2$—$CH_2$—(O)$_{x'}$—$R^{IV}$,
—$CH_2$—$CH_2$—$CH_2$—O—$CH_2$—$CH(OH)$—$CH_2OH$, and
—$CH_2$—$CH_2$—$CH_2$—O—$CH_2$—$C(CH_2OH)_2$—$CH_2$—$CH_3$, wherein
x is in a range of from 0 to 100,
x' is in a range of from 0 to 1,
y is in a range of from 0 to 100,
R' is each independently a linear or substituted alkyl or aryl group having 1 to 12 carbon atoms, where, within at least one of a radical $R^4$ and a molecule of the formula 1, mutually different substituents R' are optionally present, and
R'' is each independently a hydrogen radical or an alkyl group having 1 to 4 carbon atoms, or a group —C(O)—R''' where R'''=an alkyl radical, a group —$CH_2$—R', an alkylaryl group, the group —C(O)NH—R',
$R^{IV}$ is an optionally substituted hydrocarbon radical having 1 to 50 carbon atoms,
$R^4$ is each independently a linear, cyclic or branched, saturated or unsaturated or aromatic hydrocarbon radical having 1 to 30 carbon atoms which is optionally substituted with a group comprising heteroatoms O, N, S, P or halogen atoms and which optionally contains no primary or secondary amine functions, and
$R^5$ is each independently a radical of $R^1$, $R^2$, $R^3$ or $R^4$, characterized in that
(a) laterally epoxy-modified siloxane of formula 3

$$M_a M''''_{a1} M''_{a2} M'''_{a3} D_b D''''_{b1} D''_{b2} D'''_{b3} T_c Q_d \quad \text{(formula 3)}$$

where:
$M=(R^1{}_3SiO_{1/2})$;
$M''''=(R^{10}R^1{}_2SiO_{1/2})$;
$M''=(R^3R^1{}_2SiO_{1/2})$;
$M'''=(R^4R^1{}_2SiO_{1/2})$;
$D=(R^1{}_2SiO_{2/2})$;
$D''''=(R^{10}R^1SiO_{2/2})$;
$D''=(R^3R^1SiO_{2/2})$;
$D'''=(R^4R^1SiO_{2/2})$;
$T=(R^5SiO_{3/2})$; and
$Q=(SiO_{4/2})$,
where a, a1, a2, a3, b, b1, b2, b3, c, d, $R^3$, $R^4$ and $R^5$ have the meaning as specified under formula 1 and
$R^{10}$ is each independently an organic epoxy radical
are reacted
(b) with ammonia or instead of ammonia, with an ammonium compound which is capable of producing ammonia,
(c) in the presence of a ring-opening catalyst or at a pressure 4 bar and above
(d) at a minimum temperature of 60° C. to 150° C.

2. The method according to claim 1, wherein the epoxy-functional compound of the formula 3 comprises $R^{10}$, wherein $R^{10}$ is each independently an organic epoxy radical selected from the group consisting of $$—(CH_2)_3—O—CH_2—\underset{H}{\overset{O}{\overset{\diagup\diagdown}{C}}}—CH_2 \quad (3a)$$

-continued (3b)
$$-CH_2-CH_2-\underset{\triangle}{\bigcirc}O$$

(3c)
$$-(CH_2)_m-O-CH_2-\underset{H}{\overset{O}{C}}-CH_2$$

(3d)
(structure of epoxy-norbornane type)

(3e)
$$-CH_2-CH-\underset{R^6}{\overset{O}{\|}}C-O-R^7-\underset{H}{\overset{O}{C}}-CH_2.$$

3. The method according to claim 1, wherein said ammonia or said ammonium compound used comprises one or more selected from the group consisting of gaseous ammonia, aqueous ammonia solutions, alcoholic ammonia solutions, ammonium halides, ammonium carbonate, hydrogencarbonate, ammonium sulfate, hydrogensulfate, ammonium sulfamate, ammonium phosphate, hydrogenphosphate, dihydrogenphosphate, ammonium cyanate, ammonium carboxylates, ammonium acetate, ammonium hydrogenoxalate, oxalate, ammonium hydrogencitrate, ammonium benzoate, ammonium formate, ammonium carbamate, ammonium lactate, ammonium tartrate, ammonium succinate, hydroxylamine, hydroxylamine-O-sulfonic acid, amidosulfonic acid and urotropin.

4. A method for producing selectively primary amino group-carrying siloxanes of general formula 1 or a quaternary ammonium derivative thereof, wherein $$M_a M'_{a1} M''_{a2} M'''_{a3} D_b D'_{b1} D''_{b2} D'''_{b3} T_c Q_d \quad \text{(formula 1)}$$

where
$M=(R^1_3SiO_{1/2})$;
$M'=(R^2R^1_2SiO_{1/2})$;
$M''=(R^3R^1_2SiO_{1/2})$;
$M'''=(R^4R^1_2SiO_{1/2})$;
$D=(R^1_2SiO_{2/2})$;
$D'=(R^2R^1SiO_{2/2})$;
$D''=(R^3R^1SiO_{2/2})$;
$D'''=(R^4R^1SiO_{2/2})$;
$T=(R^5SiO_{3/2})$;
$Q=(SiO_{4/2})$;
a is in a range of from 0 to 32;
a1 is in a range of from 0 to 10;
a2 is in a range of from 0 to 32;
a3 is in a range of from 0 to 10;
b is in a range of from 0 to 600;
b1 is in a range of from 0 to 50;
b2 is in a range of from 0.1 to 20;
b3 is in a range of from 0 to 50;
c is in a range of from 0 to 20; and
d is in a range of from 0 to 20;
wherein:
if a1=2, at least one of b1, b2, b3, a2 and a3 is not 0 and at least two of the factors a2, a3, b1, b2 and b3 are not 0;
$R^1$ is each independently a linear or branched hydrocarbon radical having 1 to 30 carbon atoms or aromatic hydrocarbon radicals having 6 to 30 carbon atoms;

$R^2$ is each independently an organic radical comprising a primary amino function;

$R^3$ is each independently a radical selected from the group consisting of
—$CH_2$—$CH_2$—$CH_2$—O—($CH_2$—$CH_2O$—)$_x$—($CH_2$—$CH(R')O$—)$_y$—R'',
—$CH_2$—$CH_2$—O—($CH_2$—$CH_2O$—)$_x$($CH_2$—$CH(R')O$—)$_y$—R'',
—$CH_2$—$CH_2$—(O)$_{x'}$—$R^{IV}$,
—$CH_2$—$CH_2$—$CH_2$—O—$CH_2$—$CH(OH)$—$CH_2OH$, and
—$CH_2$—$CH_2$—$CH_2$—O—$CH_2$—$C(CH_2OH)_2$—$CH_2$—$CH_3$, wherein x is in a range of from 0 to 100,
x' is in a range of from 0 to 1,
y is in a range of from 0 to 100,
R' is each independently a linear or substituted alkyl or aryl group having 1 to 12 carbon atoms, where, within at least one of a radical $R^4$ and a molecule of the formula 1, mutually different substituents R' are optionally present, and R'' is each independently a hydrogen radical or an alkyl group having 1 to 4 carbon atoms, or a group —C(O)—R''' where R'''=an alkyl radical, a group —$CH_2$—O—R', an alkylaryl group, the group —C(O)NH—R', $R^{IV}$ is an optionally substituted hydrocarbon radical having 1 to 50 carbon atoms, $R^4$ is each independently a linear, cyclic or branched, saturated or unsaturated or aromatic hydrocarbon radical having 1 to 30 carbon atoms which is optionally substituted with a group comprising heteroatoms O, N, S, P or halogen atoms and which optionally contains no primary or secondary amine functions, and $R^5$ is each independently a radical of R', $R^2$, $R^3$ or $R^4$, characterized in that (a) laterally epoxy-modified siloxane of formula 3

$$M_a M''''_{a1} M''_{a2} M'''_{a3} D_b D''''_{b1} D''_{b2} D'''_{b3} T_c Q_d \quad \text{(formula 3)}$$

where:
$M=(R^1_3SiO_{1/2})$;
$M''''=(R^{10}R^1_2SiO_{1/2})$;
$M''=(R^3R^1_2SiO_{1/2})$;
$M'''=(R^4R^1_2SiO_{1/2})$;
$D=(R^1_2SiO_{2/2})$;
$D''''=(R^{10}R^1SiO_{2/2})$;
$D''=(R^3R^1SiO_{2/2})$;
$D'''=(R^4R^1SiO_{2/2})$;
$T=(R^5SiO_{3/2})$; and
$Q=(SiO_{4/2})$,
where a, a1, a2, a3, b, b1, b2, b3, c, d, $R^3$, $R^4$ and $R^5$ have the meaning as specified under formula 1 and
$R^{10}$ is each independently an organic epoxy radical
are reacted (b) with ammonia or instead of ammonia, with an ammonium compound which is capable of producing ammonia, (c) in the presence of a ring-opening catalyst or at a pressure above 1 bar (d) at a minimum temperature of 50° C. to 150° C.,
further comprising passing gaseous ammonia in a pressureless manner through a mixture comprising the epoxy-functional compound.

5. The method according to claim 1, comprising carrying out the reaction at a pressure from 4 to 50 bar.

6. The method according to claim 1, comprising carrying out the reaction at a pressure from 5-20 bar.

7. The method according to claim 1, comprising carrying out the reaction at a pressure from 5-50 bar.

\* \* \* \* \*

UNITED STATES PATENT AND TRADEMARK OFFICE
CERTIFICATE OF CORRECTION

PATENT NO.       : 9,695,202 B2
APPLICATION NO.  : 14/548724
DATED            : July 4, 2017
INVENTOR(S)      : Frauke Henning, Wilfried Knott and Horst Dudzik Page 1 of 1

It is certified that error appears in the above-identified patent and that said Letters Patent is hereby corrected as shown below:

In the Claims

Column 16,
Line 36, "a radical of R'," should read -- a radical of $R^1$ --

Signed and Sealed this
Fifth Day of September, 2017

Joseph Matal
*Performing the Functions and Duties of the*
*Under Secretary of Commerce for Intellectual Property and*
*Director of the United States Patent and Trademark Office*